United States Patent
Shimizu

(10) Patent No.: US 9,237,863 B2
(45) Date of Patent: Jan. 19, 2016

(54) PERSONAL AUTHENTICATION APPARATUS AND BODY WEIGHT/BODY COMPOSITION METER

(71) Applicant: OMRON HEALTHCARE CO., LTD., Muko-shi, Kyoto (JP)

(72) Inventor: Satoe Shimizu, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 14/404,569

(22) PCT Filed: Apr. 30, 2013

(86) PCT No.: PCT/JP2013/062593
§ 371 (c)(1),
(2) Date: Nov. 28, 2014

(87) PCT Pub. No.: WO2013/179848
PCT Pub. Date: Dec. 5, 2013

(65) Prior Publication Data
US 2015/0109105 A1    Apr. 23, 2015

(30) Foreign Application Priority Data
May 28, 2012   (JP) .................................. 2012-121041

(51) Int. Cl.
*A61B 5/117*    (2006.01)
*A61B 5/053*    (2006.01)
(Continued)

(52) U.S. Cl.
CPC ............... *A61B 5/117* (2013.01); *A61B 5/0537* (2013.01); *A61B 5/4872* (2013.01); *A61B 5/4875* (2013.01); *G01G 19/50* (2013.01); *A61B 5/0002* (2013.01)

(58) Field of Classification Search
CPC .... A61B 5/117; A61B 5/4872; A61B 5/0537; A61B 5/0002; A61B 5/4875; G01G 19/50
USPC ............. 340/5.82, 5.52; 600/509, 547; 177/4, 177/245, 25.19
See application file for complete search history.

(56) References Cited

U.S. PATENT DOCUMENTS

2005/0171451 A1    8/2005   Yeo et al.

FOREIGN PATENT DOCUMENTS

| JP | A-2003-315142 | 11/2003 |
| JP | A-2005-228315 | 8/2005 |

(Continued)

OTHER PUBLICATIONS

International Search Report issued in International Application No. PCT/JP2013/062593 mailed Jun. 11, 2013.
(Continued)

*Primary Examiner* — Nabil Syed
(74) *Attorney, Agent, or Firm* — Oliff PLC

(57) ABSTRACT

A personal authentication apparatus includes: an acquisition unit that acquires a measurement result including body weight and body impedance; a calculation unit configured to, based on the measurement result acquired by the acquisition unit and personal information, calculate a calculation value relating to body composition that is less susceptible to temporal variation than body water amount; a storage unit configured to store the body weight, the personal information, and the calculation value in association with measurement subject specification information that specifies the measurement subject; a comparison unit configured to compare the most recent calculation value and a new calculation value; and a measurement subject specification unit configured to, based on a difference between calculation values, specify which of the pieces of measurement subject specification information stored in the storage unit corresponds to the measurement result acquired by the acquisition unit.

9 Claims, 7 Drawing Sheets

(51) Int. Cl.
*A61B 5/00* (2006.01)
*G01G 19/50* (2006.01)

(56) References Cited

FOREIGN PATENT DOCUMENTS

| JP | A-2005-296154 | 10/2005 |
| JP | A-2008-279181 | 11/2008 |
| JP | A-2009-213528 | 9/2009 |
| JP | A-2011-24732 | 2/2011 |

OTHER PUBLICATIONS

Written Opinion of the International Searching Authority issued in International Application No. PCT/JP2013/062593 mailed Jun. 11, 2013.

FIG. 6A

|  |  | MEMORY ||||||
|  |  | STORED MEASUREMENT VALUE ||| PERSONAL INFORMATION |||
|  |  | BODY WEIGHT | BODY WEIGHT - FFM | BODY COMPOSITION (BODY FAT PERCENTAGE) | AGE | HEIGHT | SEX |
| --- | --- | --- | --- | --- | --- | --- | --- |
| REGISTRATION NUMBER 1 | REGISTERED | 54.35kg | 35.30kg | 21.2% | 45 | 160.5 | F |
| REGISTRATION NUMBER 2 | REGISTERED | 80.80kg | 60.90kg | 26.5% | 28 | 173.5 | M |
| REGISTRATION NUMBER 3 | UNREGISTERED | — | — | — | — | — | — |
| REGISTRATION NUMBER 4 | UNREGISTERED | — | — | — | — | — | — |
| GUEST |  | — | — | — | — | — | — |

FIG. 6B

|  |  | MEMORY ||||||
|  |  | STORED MEASUREMENT VALUE ||| PERSONAL INFORMATION |||
|  |  | BODY WEIGHT | BODY WEIGHT - FFM | BODY COMPOSITION (BODY FAT PERCENTAGE) | AGE | HEIGHT | SEX |
| --- | --- | --- | --- | --- | --- | --- | --- |
| REGISTRATION NUMBER 1 | REGISTERED | 53.25kg | 34.20kg | 21.0% | 45 | 160.5 | F |
| REGISTRATION NUMBER 2 | REGISTERED | 80.80kg | 60.90kg | 26.5% | 28 | 173.5 | M |
| REGISTRATION NUMBER 3 | UNREGISTERED | — | — | — | — | — | — |
| REGISTRATION NUMBER 4 | UNREGISTERED | — | — | — | — | — | — |
| GUEST |  | — | — | — | — | — | — |

FIG. 6C

|  |  | MEMORY ||||||
|  |  | STORED MEASUREMENT VALUE ||| PERSONAL INFORMATION |||
|  |  | BODY WEIGHT | BODY WEIGHT - FFM | BODY COMPOSITION (BODY FAT PERCENTAGE) | AGE | HEIGHT | SEX |
| --- | --- | --- | --- | --- | --- | --- | --- |
| REGISTRATION NUMBER 1 | REGISTERED | 54.35kg | 35.30kg | 21.2% | 45 | 160.5 | F |
| REGISTRATION NUMBER 2 | REGISTERED | 80.80kg | 60.90kg | 26.5% | 28 | 173.5 | M |
| REGISTRATION NUMBER 3 | UNREGISTERED | — | — | — | — | — | — |
| REGISTRATION NUMBER 4 | REGISTERED | 53.25kg | 31.20kg | 20.8% | 23 | 162.5 | F |
| GUEST |  | — | — | — | — | — | — |

FIG. 6D

|  |  | MEMORY ||||||
|  |  | STORED MEASUREMENT VALUE ||| PERSONAL INFORMATION |||
|  |  | BODY WEIGHT | BODY WEIGHT - FFM | BODY COMPOSITION (BODY FAT PERCENTAGE) | AGE | HEIGHT | SEX |
| --- | --- | --- | --- | --- | --- | --- | --- |
| REGISTRATION NUMBER 1 | REGISTERED | 54.25kg | 35.20kg | 21.0% | 45 | 160.5 | F |
| REGISTRATION NUMBER 2 | REGISTERED | 80.80kg | 60.90kg | 26.5% | 28 | 173.5 | M |
| REGISTRATION NUMBER 3 | UNREGISTERED | — | — | — | — | — | — |
| REGISTRATION NUMBER 4 | REGISTERED | 53.25kg | 31.20kg | 20.8% | 23 | 162.5 | F |
| GUEST |  | 65.25kg | 42.20kg | 25.2% | 25 | 157.0 | F |

# PERSONAL AUTHENTICATION APPARATUS AND BODY WEIGHT/BODY COMPOSITION METER

TECHNICAL FIELD

The present invention relates to a personal authentication apparatus that performs authentication regarding which individual among registered individuals is using the apparatus, and relates to a body weight/body composition meter.

BACKGROUND ART

Conventionally, in body weight/body composition meters, personal information such as the age, height, and sex of a measurement subject is used for calculating body composition. Accordingly, before body composition is measured, a personal specification number associated with personal information that corresponds to the current instance of measurement needs to be selected from among the registered personal specification numbers. However, due to the fact that a task of designating a personal specification number that corresponds to the measurement subject from among the registered personal specification numbers and a task of storing the personal specification number are performed during the body composition calculation process, it is necessary for the measurement subject to designate and remember the personal specification number. In view of this, for example, Patent Document 1 discloses a body weight/body composition meter that includes a personal recognition function according to which the personal specification number corresponding to the measurement subject is automatically recognized from among registered personal specification numbers.

CITATION LIST

Patent Literature

Patent Document 1: JP 2009-213528A

SUMMARY OF INVENTION

Technical Problem

With the personal recognition method disclosed in Patent Document 1, a body weight value and a body electrical impedance value that were measured in the past, and a body weight value and a body electrical impedance value that were measured in the current instance are compared, and it is determined that the value among the values measured in the past that is the closest to the value measured in the current instance belongs to the measurement subject who was measured in the current instance. The body weight value and the body electrical impedance value that were used for personal recognition in Patent Document 1 are dependent on the amount of water contained in the body, and the amount of water contained in the body has a tendency to vary over the course of a day or a week. Accordingly, the personal recognition method disclosed in Patent Document 1 is problematic in that the accuracy of personal recognition is low since the body weight value and the body electrical impedance value used for personal recognition tend to vary over the course of a day and over the course of a week.

In view of this, it is an object of the present invention to provide a body weight/body composition meter and a personal authentication apparatus that is not susceptible to temporal variation and is capable of performing personal recognition with a high level of accuracy.

Solution to Problem

To resolve the foregoing problem, the personal authentication apparatus according to an aspect of the present invention includes: an acquisition unit configured to acquire body weight and body impedance of a measurement subject; a first operation unit for performing an operation of inputting personal information that includes at least one of age, height, and sex that are specific to the measurement subject; a calculation unit configured to, based on a measurement result that includes the body weight and the body impedance acquired by the acquisition unit, and the personal information input using the first operation unit, calculate a calculation value relating to body composition that is less susceptible to temporal variation than body water amount; a storage unit configured to store at least the body weight, the personal information, and the calculation value in association with measurement subject specification information that specifies the measurement subject; a comparison unit that compares a calculation value that was most recently stored in the storage unit and a new calculation value that is newly calculated by the calculation unit; and a measurement subject specification unit configured to, based on the difference between calculation values obtained by comparing with the comparison unit, specify which of the pieces of measurement subject specification information stored in the storage unit corresponds to the measurement result acquired by the acquisition unit.

Among calculation values relating to compositional elements that are part of the body, such as the body fat mass (percentage), muscle mass (percentage), fat-free mass, bone mass, and water amount, the "calculation value relating to body composition that is less susceptible to temporal variation than body water amount" refers to calculation values such as body fat mass (percentage) or muscle mass (percentage) for example, and not calculation values such as water amount, which tends to vary over a short amount of time, such as a day or a week.

With the personal authentication apparatus of the invention, the calculation value relating to body composition that is less susceptible to temporal variation than the body water amount is calculated by the calculation unit based on measurement results including the body weight and body impedance of the measurement subject (typically refers to a user of the body weight/body composition meter. The same follows below.) acquired by the acquisition unit, and based on the personal information input using the first operation unit. The storage unit stores the body weight, the personal information, and the calculation value in association with the measurement subject specification information that specifies the measurement subject. The comparison unit obtains the difference between calculation values by comparing a calculation value that was most recently stored, and a new calculation value that is newly calculated by the calculation unit. Also, based on the difference between the calculation values, the measurement subject specification unit specifies which of the stored pieces of measurement subject specification information corresponds to the measurement result acquired by the acquisition unit. An individual is authenticated (specified) using the specified measurement subject specification information.

With the personal authentication apparatus of the invention, the target of comparison is the calculation value relating to body composition that is less susceptible to temporal variation than the body water amount. For this reason, temporal variation is less likely to occur, and personal recognition can be performed with higher accuracy than in the case where the target of comparison is the body weight and the body impedance, which are likely to vary over a short amount of time such as a day or a week due to the influence of the water amount.

With a personal authentication apparatus according to an embodiment, a plurality of pieces of the measurement subject specification information are stored in the storage unit.

With the personal authentication apparatus according to the embodiment, it is possible to specify the corresponding piece of measurement subject specification information from among of the plurality of pieces of measurement subject specification information stored in the storage unit.

With the personal authentication apparatus according to an embodiment, the measurement subject specification unit selects the measurement subject specification information corresponding to the calculation value with the smallest difference.

With the personal authentication apparatus of the embodiment, it is sufficient that the measurement subject specification information corresponding to the calculation value with the smallest difference is specified by narrowing down the limited range of pieces of measurement subject specification information stored in the storage unit, and therefore specification processing performed by the measurement subject specification unit is simplified and sped up.

With a personal authentication apparatus according to an embodiment, in the case of no specification by the measurement subject specification unit, the corresponding body weight, personal information, and calculation value are deleted from the storage unit.

With the personal authentication apparatus according to the embodiment, if there is no specification, and body weight, personal information, and a calculation value that are not needed are left in the storage unit, there is a risk that they will be confused with other information. In view of this, by deleting them from the storage unit, it is possible to prevent a negative influence such as that described above.

With the personal authentication apparatus according to an embodiment, the calculation value relating to the body composition is obtained by subtracting fat-free mass from the body weight.

With the personal authentication apparatus according to the embodiment, among the calculation values relating to body composition that are less susceptible to temporal variation than the body water amount, it is possible to use a calculation value obtained by subtracting the fat-free mass from the body weight, or in other words, the body fat mass.

With the personal authentication apparatus according to an embodiment: the calculation value relating to body composition is muscle mass.

With the personal authentication apparatus of the embodiment, among the calculation values relating to body composition that are less susceptible to temporal variation than the body water amount, it is possible to use the muscle mass.

The personal authentication apparatus according to an embodiment further includes: a display unit configured to display the measurement subject specification information; and a display control unit configured to perform control such that the measurement subject specification information is displayed on the display unit.

With the personal authentication apparatus of the embodiment, user-friendliness with respect to the measurement subject is improved, and it is possible to prevent incorrect body weight, personal information, and calculation values from being stored in the storage unit due to the measurement subject checking the displayed content.

With the personal authentication apparatus according to an embodiment, the display control unit causes the display unit to display confirmation information for prompting checking of correctness with regard to the measurement subject specification information, and the personal authentication apparatus further includes a second operation unit for performing an operation of input as to whether to accept or correct the measurement subject specification information, based on the confirmation information displayed on the display unit.

With the personal authentication apparatus of the embodiment, by performing an operation of checking the content of the measurement subject specification information and an operation of accepting or correcting the measurement subject specification information, user-friendliness with respect to the measurement subject is improved, and it is possible to prevent incorrect body weight, personal information, and calculation values from being stored in the storage unit due to the measurement subject checking the displayed content.

A body weight/body composition meter according to another aspect of the invention includes: the personal authentication apparatus according to any one of claims 1 to 8.

With the body weight/body composition meter of the invention, temporal variation is less likely to occur, and personal recognition can be performed with a high accuracy.

Advantageous Effects of the Invention

As is evident from the above description, with the personal authentication apparatus and the body weight/body composition meter of the present invention, calculation values relating to body composition, which are less likely to vary over time than the body water amount, are compared when the measurement subject is to be specified, and therefore, temporal variation is less likely to occur and personal recognition can be performed at a higher accuracy than with an apparatus that compares body weight and body impedance, which are likely to vary over a short amount of time such as a day or a week due to the influence of the water amount.

BRIEF DESCRIPTION OF DRAWINGS

FIGS. 6A-6D are diagrams illustrating content stored in a storage unit. FIG. 6A shows a state before measurement, FIG. 6B shows a state after completion of personal authentication, FIG. 6C shows a state of being registered as a different, unregistered individual, and FIG. 6D shows a state of being recognized as a guest.

FIG. 7A shows a display screen for measurement subject specification information, FIG. 7B shows a display screen for showing measurement subject specification information, personal information, and measurement results that have been specified, FIG. 7C is a display screen for modified measurement subject specification information, and FIG. 7D is a screen for prompting input of personal information relating to the modified measurement subject specification information.

Description of Embodiments

Hereinafter, preferred embodiments of the present invention will be described in detail with reference to the drawings.

A body weight/body composition meter 10 that includes a personal authentication apparatus 1 according to an embodiment of the invention has a function of measuring the body weight and body impedance of a person who is a measurement subject (hereinafter referred to as "measurement subject"). Also, as will be described later, body composition is calculated based on the body weight, body impedance, and personal information including at least one of age, height, and sex that are specific to the measurement subject. The calculated body composition represents the percentage or mass of components that compose the body (structures that make up the body), which are, for example, body fat percentage, muscle percentage, fat-free mass, body fat mass, muscle mass, bone mass, and water amount.

Figure 1:
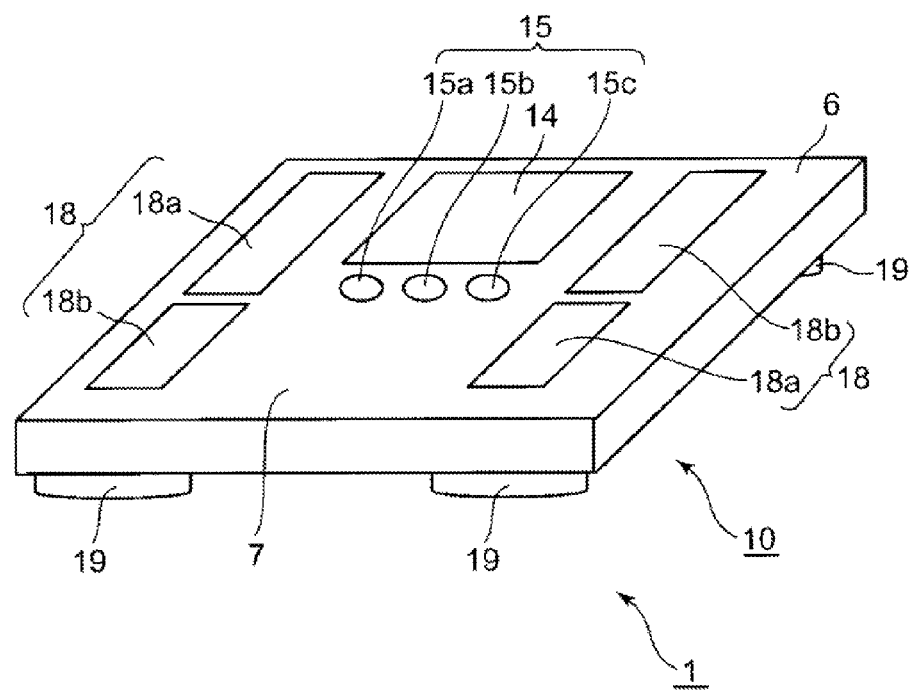
FIG. 1 is a perspective view showing a body weight/body composition meter that includes a personal authentication apparatus according to the invention.

In FIG. 1, the body weight/body composition meter 10 that includes the personal authentication apparatus 1 includes a mounting surface 7 formed on the upper surface of a housing 6, multiple electrodes 18 provided on the mounting surface 7, and multiple load cells (body weight sensors) 19 that are arranged in corner portions on the lower portion of the housing 6. In order to measure the body impedance of the measurement subject, the electrodes 18 include electrodes 18a and 18b for applying a constant current to the body, and electrodes 18c and 18d for measuring the voltage derived from the body at the time of applying the current. The load cells (body weight sensors) 19 are, for example, strain gauges. In FIG. 1 shows a configuration in which four load cells (body weight sensors) 19 are provided, but two or one load cell (body weight sensor) 19 may be provided, as long as body weight can be detected accurately.

A display unit 14 and an operation unit 15 are arranged on the mounting surface 7.

The display unit 14 includes a display screen (e.g., LCD (Liquid Crystal Display), EL (Electroluminescence) display, or the like). The display unit 14 displays personal information (age, height, and sex), body weight and body composition, measurement subject specification information (a registration number is typically used, but characters such as letters, symbols, or a combination of both may be used, and hereinafter, it will be simply referred to as "measurement subject specification information"), and the like of the measurement subject on the display screen. The display screen is controlled by a control unit 11 that functions as a display control unit. A configuration is also possible in which the display unit 14 is provided separately from the housing 6 and mutual communication therebetween is possible using a wired or wireless method.

For example, the operation unit 15 includes a power supply switch 15a that is operated in order to switch on/off a power supply of the body weight/body composition meter 10, a first operation switch 15b serving as a first operation unit for receiving input of personal information (age, height, and sex) of a measurement subject, and a second operation switch 15c serving as a second operation unit for specifying which of the multiple registered measurement subjects the current instance of measurement is for. Note that as long as the installation location of the operation unit 15 is a location at which operation by the measurement subject is possible, it is not limited to the location shown in FIG. 1, and for example, it can be installed on a side circumferential surface of the housing of the body weight/body composition meter 10. Also, the operation unit 15 can be a mouse and keyboard that are provided separately from the housing 6, and are configured such that mutual communication therebetween is possible using a wired or wireless method.

Next, the hardware configuration of the body weight/body composition meter 10 that includes the personal authentication apparatus 1 according to an embodiment of the invention will be described with reference to FIG. 2.

Figure 2:
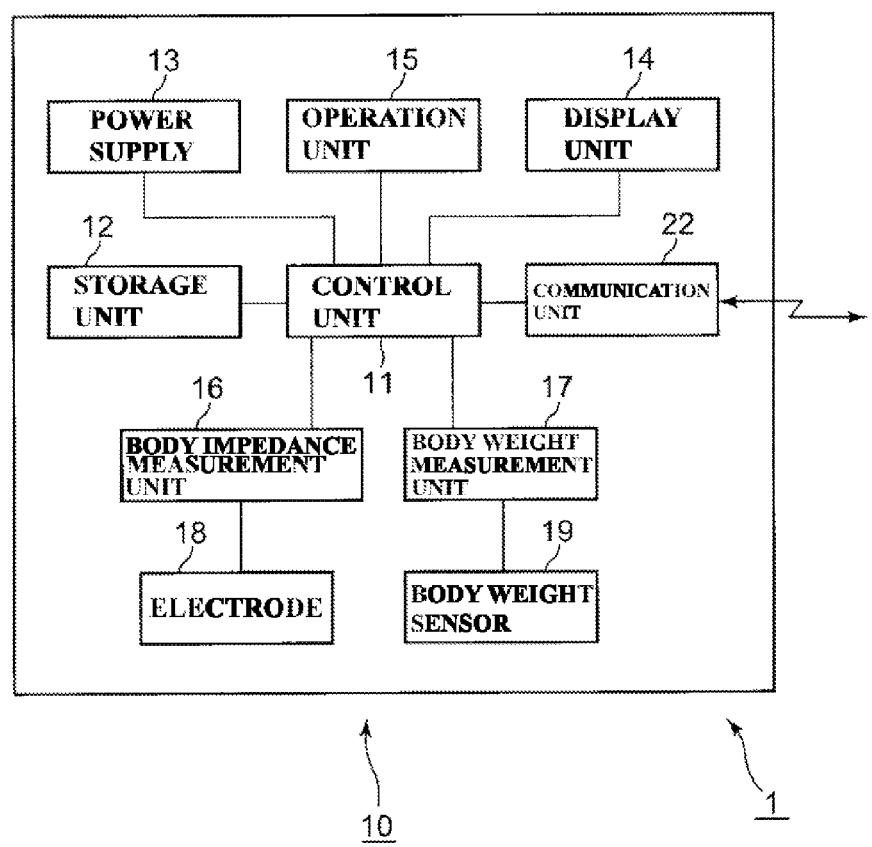
FIG. 2 is a functional block diagram showing a configuration of the body weight/body composition meter that includes the personal authentication apparatus.

FIG. 2 shows the body weight/body composition meter 10 that includes the personal authentication apparatus 1 of the present invention as a configuration that is available on a network as well. The body weight/body composition meter 10 is configured to be able to mutually communicate with a server (not shown) via a network (not shown) using a wired or wireless method.

As shown in FIG. 2, the body weight/body composition meter 10 includes the control unit 11, a storage unit 12, a power supply 13, a display unit 14, an operation unit 15, a body impedance measurement unit 16, a body weight measurement unit 17, and a communication unit 22.

The control unit 11 includes a CPU (Central Processing Unit) and auxiliary circuits thereof, controls the units of the body weight/body composition meter 10, and executes various types of processing according to programs and data stored in the storage unit 12. In other words, data input from the operation unit 15 and the communication unit 22 is processed, and the processed data is stored in the storage unit 12, displayed on the display unit 14, or output from the communication unit 22.

Due to the CPU executing a program, the control unit 11 functions as a body composition calculation unit by calculating a body composition indicating the percentage or mass of components that compose the body (structures that make up the body) based on the result of the current instance of measurement, including the body weight and body impedance, and based on the personal information (age, height, and sex) that is specific to the measurement subject that was loaded from the storage unit 12.

Due to the CPU executing a program, the control unit 11 functions as a calculation unit that calculates a calculation value by calculating a calculation value (body fat amount or muscle mass calculated using "body weight—fat-free mass") relating to body composition, which has little temporal variation in comparison to the body water amount, based on the result of the current instance of measurement, including the body weight and body impedance, and based on the personal information (age, height, and sex) that is specific to the measurement subject that was loaded from the storage unit 12.

The control unit 11 furthermore functions as a comparison unit that compares a new calculation value that is newly calculated by the control unit 11 serving as the calculation unit, and a past calculation value that was most recently stored in the storage unit, and calculates a difference between the two calculation values for each of the registered individuals.

The control unit 11 furthermore functions as a measurement subject specification unit that, based on the difference between the calculation values, specifies which piece of measurement subject specification information stored in the storage unit 12 corresponds to the result of the current instance of measurement that was measured and obtained by the body impedance measurement unit 16 and the body weight measurement unit 17 functioning as acquisition units. Specifically, the control unit 11 serving as the measurement subject specification unit selects the smallest difference among the calculated differences between the calculation values and specifies the measurement subject specification information corresponding to the calculation value with the smallest difference.

The control unit 11 furthermore functions as a display control unit that performs control of displaying the measurement subject specification information, personal information (age, height, and sex), measurement results (e.g., body weight), the calculated body composition (e.g., body fat mass or muscle mass), or a screen for checking correctness on the display unit 14.

The storage unit 12 includes a RAM (Random Access Memory) that is used as a work region needed for executing a program with the control unit 11, and a ROM (Read Only Memory) for storing basic programs that are to be executed by the control unit 11. Also, a semiconductor memory (memory card, SSD (Solid State Drive)) or the like can be used as the storage medium for an auxiliary storage apparatus for supplementing the storage region of the storage unit 12.

The storage unit 12 stores the personal information of the measurement subject (sex, age, height), the body weight of the measurement subject, and the calculation value relating to the body composition of the measurement subject in the storage unit 12 in a time series for each measurement subject. At this time, the personal information, body weight, and calculation value are stored in association with the measurement subject specification information for specifying the measurement subject. The storage unit 12 has enough capacity to register information for multiple people. The storage unit 12 normally stores measurement subject specification information, personal information (age, height, and sex), measurement results (e.g., body weight), the calculated body composition (e.g., body fat mass or muscle mass), and calculation values (body fat mass (percentage), muscle mass (percentage)) related to body composition, which are less likely to have temporal variation than the body water amount, for the registered individuals.

As described above, the operation unit 15 is constituted by multiple switches, such as a power supply switch 15a, a first operation switch 15b, and a second operation switch 15c for example, but it can be constituted by a touch panel, for example. An operation signal input by the measurement subject via the operation unit 15 is input to the control unit 11 as an operation signal that indicates an operation.

The display unit 14 and the operation unit 15 can also be parts of a stationary information processing terminal such as a desktop-type personal computer, an information processing terminal with portability, such as a note-type personal computer, or a mobile information processing terminal such as a mobile phone, smartphone, or tablet, for example, which includes a control unit, a storage unit, a power supply, a display unit, an operation unit, and a communication unit.

The body impedance measurement unit 16 measures the body impedance of the measurement subject by applying a current to the body from current application electrodes (18a and 18b) for measuring the body impedance of the measurement subject and detecting a voltage using voltage detection electrodes (18c and 18d). The body weight measurement unit 17 is a body weight sensor that measures the body weight of the measurement subject by detecting change in the resistance value detected by the strain gauge (not shown). The body impedance measurement unit 16 and the body weight measurement unit 17 function as acquisition units that acquire measurement results by measuring the body impedance and body weight of the measurement subject.

The communication unit 22 is used for transmitting data generated by the control unit 11 and data stored in the storage unit 12 to the server and receiving data generated by the control unit of the server (not shown) and data stored in the storage unit of the server (not shown).

Figure 3:
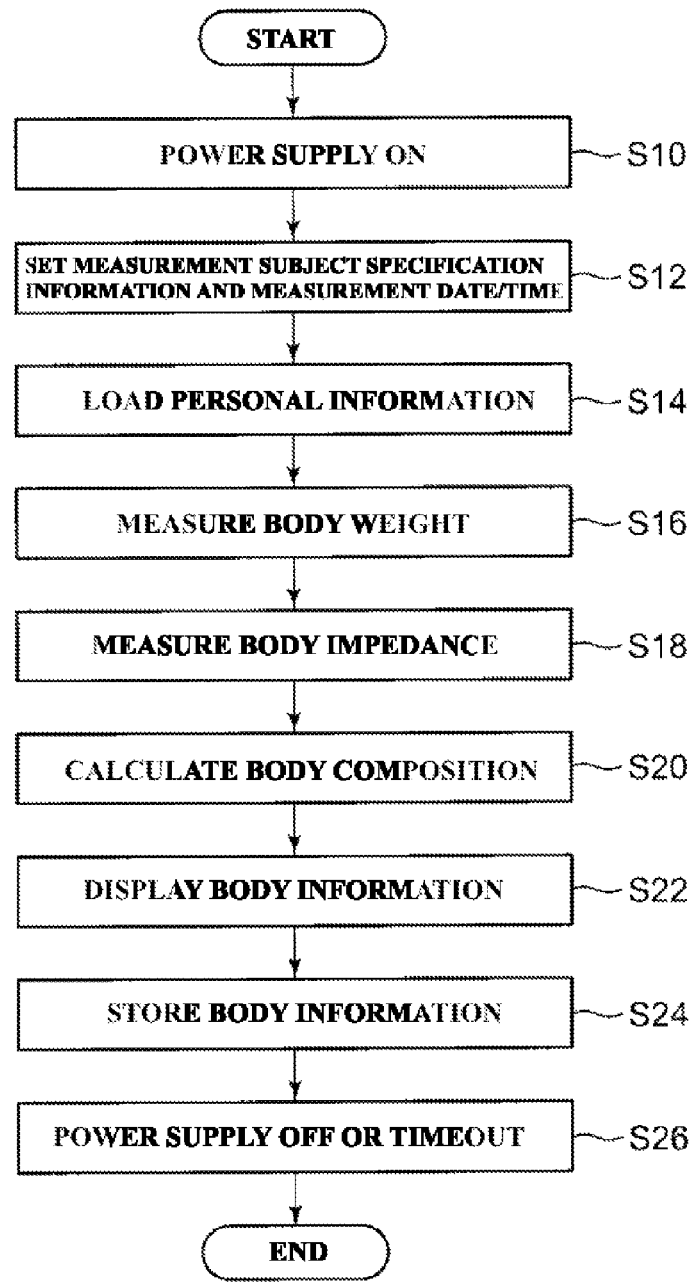
FIG. 3 is a diagram showing an overall operational flow for the body weight/body composition meter that includes the personal authentication apparatus.

Next, the overall operation of the body weight/body composition meter 10 that includes the personal authentication apparatus 1 according to an embodiment of the present invention will be described with reference to FIG. 3. The processing shown in the flowchart in FIG. 3 is executed by the CPU of the control unit 11 reading out a program stored in the ROM of the storage unit 12 and controlling the constituent elements shown in FIG. 2.

If the measurement subject switches on the power supply switch 15a of the body weight/body composition meter 10 (step S10), the control unit 11 executes calibration processing for the body weight measurement unit 17. After calibration is complete, it is possible to perform settings relating to the measurement subject specification information of the measurement subject who is to use the apparatus, and the measurement date/time (step S12). If the measurement subject specification information is designated by the measurement subject, the control unit 11 loads the personal information (age, height, and sex) associated with the measurement subject specification information from the storage unit 12 (step S14).

The measurement subject steps onto the mounting surface 7 such that the bottoms of the measurement subject's feet are in contact with the electrodes 18a, 18b, 18c, and 18d on the body weight/body composition meter 10. Then, when the measurement subject maintains a still measurement posture, the body weight measurement unit 17 performs body weight measurement (step S16). Also, the body impedance measurement unit 16 performs body impedance measurement (step S18). The measurement result acquired according to the measurement is input to the control unit 11.

The control unit 11 serving as the body composition calculation unit calculates various types of body composition based on the body weight and impedance measurement results and the measurement subject specification information loaded from the storage unit 12 (step S20).

That is to say, the control unit 11 uses the body weight and the body impedance of the measurement subject, and the personal information (age, height, and sex) of the measurement subject to calculate the body composition of the entire body or a particular site of the measurement subject in accordance with a publicly-known algorithm.

The body composition that is calculated is, for example, a body fat mass (percentage), such as visceral fat mass (percentage) or subcutaneous fat mass (percentage), a muscle mass (percentage) such as skeletal muscle mass (percentage), water amount, or the like. These body compositions can also be calculated not only for the entire body, but for a particular site, such as an arm, the torso, or a leg. Furthermore, it is also possible to generate guide information that is beneficial for diet and maintaining health, such as baseline metabolism, body-mass index, and body age, based on the calculation results. The body composition calculation can be performed using a publicly-known method, and for example, the fat-free mass (FFM) and the body fat percentage (% FAT) of the entire body can be calculated using Equation (1) and Equation (2) below.

$$\% \text{FAT} = [(W - \text{FFM})/W] \times 100 \tag{1}$$

$$\text{FFM} = a \times H^2 / Z_w + b \times W + c \times Ag + d \tag{2}$$

(Here, FFM is fat-free mass, W is weight, H is height, $Z_w$ is impedance, Ag is age, and a to d are constants.)

The control unit 11 displays body information such as the measured body weight and the calculated body composition on the display unit 14 (step S22). The measurement subject can check the measurement results based on the body information displayed on the display unit 14. The control unit 11 stores body information such as the body weight and body composition of the measurement subject in the storage unit 12 in association with the measurement subject specification information of the measurement subject and the measurement date/time information (time stamp) (step S24). If there is a limit to the amount that can be stored in the storage unit 12, the oldest pieces of body information and measurement date/time information is deleted, and the newest pieces of body information and measurement date/time information are added.

If the measurement subject switches off the power supply switch 15a of the body weight/body composition meter 10, or the control unit 11 detects that an input operation has not been performed for a predetermined amount of time or longer, the control unit 11 switches off the power supply of the body weight/body composition meter 10 (step S26). Accordingly, the series of basic operations in the body weight/body composition meter 10 ends.

Figure 4:
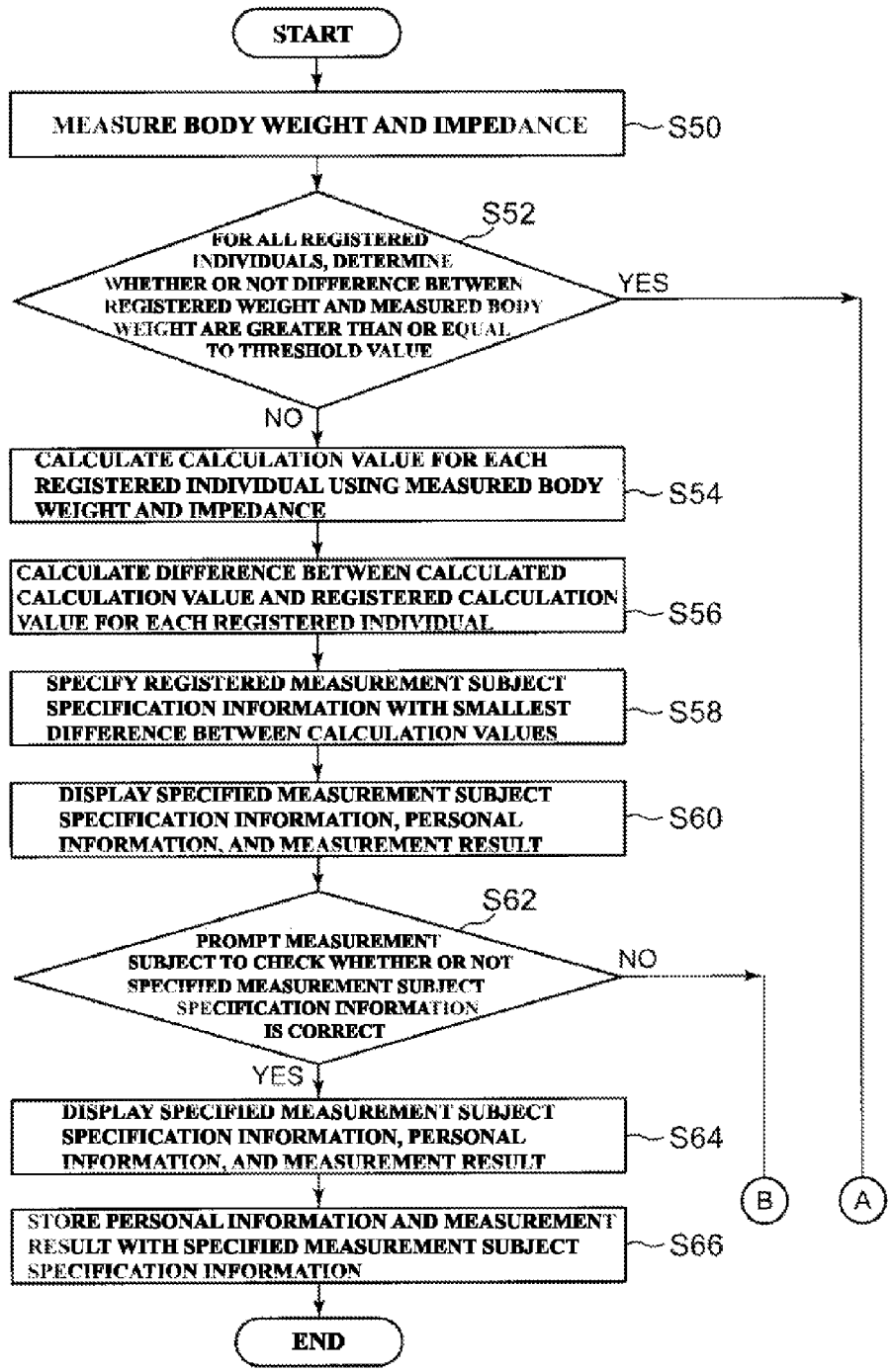
FIG. 4 is a diagram showing a characteristic operational flow for the body weight/body composition meter that includes the personal authentication apparatus.

Next, processing operations for personal authentication in the personal authentication apparatus 1 according to an embodiment of the invention will be described in detail with reference to FIGS. 4 to 7. The processing operations shown in the flowchart in FIG. 4 are executed by the CPU of the control unit 11 reading out a program stored in the ROM of the storage unit 12 and controlling the constituent elements shown in FIG. 2.

First, content such as that shown in FIG. 6(A), for example, is stored in the storage unit 12 before the processing operations for personal authentication are performed. That is to say that in FIG. 6(A), for example, registration numbers 1 and 2 have already been registered, and body information, namely body weight that was measured in the past, "body weight—FFM (fat-free mass)" that was calculated in the past, and body composition such as the body fat percentage, and personal information, namely age, height, and sex, are all stored in the storage unit 12. Here, the unit for height is cm. Regarding sex, F represents female and M represents male. Also, nothing has been registered in registration numbers 3 and 4, and the fields for body information and personal information are blank. Results for a guest are calculated and displayed temporarily, and therefore the items for body information and personal information are not stored and the fields are blank.

1) When the power supply switch 15a of the body weight/body composition meter 10 is switched on by the measurement subject, the body weight measurement unit 17 and the body impedance measurement unit 16 measure the body weight and the body impedance respectively of the measurement subject (step S50). As an example of the results of the current instance of measurement, which do not limit the invention, the body weight is 53.25 kg and the body impedance is 445 Ω. When both measurements are complete, the control unit 11 determines whether or not the difference between the registered body weight and the body weight measured in the current instance is greater than or equal to a threshold value, for each registered piece of measurement subject specification information (step S52). Here, the threshold value for the body weight difference is 10 kg, for example. In step S52, the reason the difference between the registered body weight and the body weight measured in the current instance is compared and considered is because it is more reasonable to think of the current measurement subject as being unregistered (a guest) if there is clearly a significant body weight difference.

Case of being recognized from among registered pieces of measurement subject specification information 2) If the control unit 11 determines in step S52 that the difference between the registered body weight and the body weight measured in the current instance is smaller than a threshold value, the control unit 11 serving as a calculation unit uses the measurement results for body weight and body impedance obtained according to the current measurement, so as to calculate the calculation value relating to body composition that is less susceptible to temporal variation than the body water amount for each registered piece of measurement subject specification information (step S54). Here, the calculation value is calculated using the personal information (age, height, and sex) of each registered individual. Also, the calculation value relating to body composition that is less susceptible to temporal variation than the body water amount (referred to below as simply "calculation value") is the body fat mass or the muscle mass calculated using "body weight—FFM (Fat Free Mass)".

3) The control unit 11 serving as the comparison unit compares the new calculation value that was newly obtained using the current calculation and the most recent past calculation value stored in the storage unit 12, and calculates the difference between the two calculation values for each registered piece of measurement subject specification information (step S56).

4) The control unit 11 serving as the measurement subject specification unit selects the calculation value with the smallest difference among the calculated differences between calculation values and specifies the measurement subject specification information corresponding to the calculation value with the smallest difference (step S58).

5) The control unit 11 serving as the display control unit causes the display unit 14 to display the specified measurement subject specification information, the personal information, and/or the measurement result (typically body weight) (step S60).

6) The control unit 11 functioning as the display control unit causes the display unit 14 to display a confirmation screen for prompting the measurement subject to check whether or not the specified measurement subject specification information is correct (step S62).

Figure 7A:
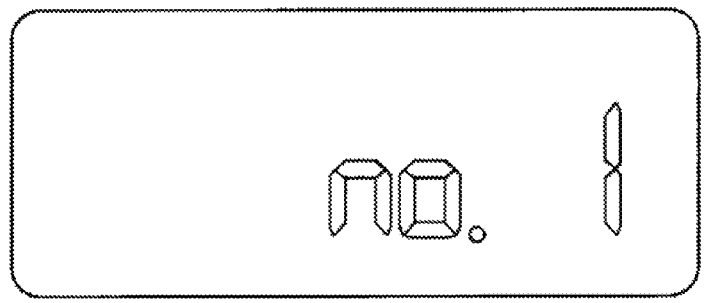
FIGS. 7A-7D are diagrams illustrating content displayed on a display unit.
Figure 7B:
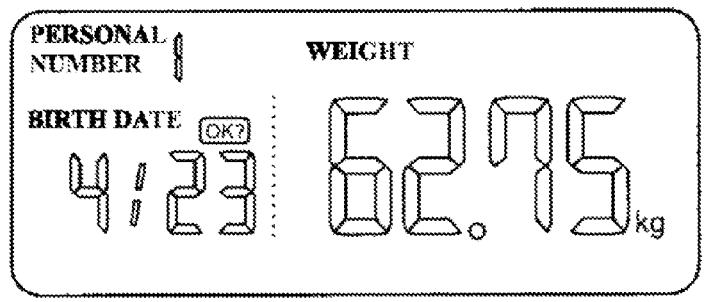

7) If input such that the specified measurement subject specification information is correct is received from the operation unit 15 in step S62, the control unit 11 functioning as the display control unit causes the display unit 14 to display the specified measurement subject specification information, the personal information, and the measurement result (typically body weight) for re-confirmation (step S64). For example, a screen such as that shown in FIGS. 7(A) and (B) is displayed. FIG. 7(A) shows that the registration number (personal number) serving as the measurement subject specification information is 1. FIG. 7(B) shows that the body weight of the individual of registration number 1 is 62.75 kg, and the like.

8) The control unit 11 stores body information such as the body weight and body composition of the measurement subject acquired according to the current instance of measurement in the storage unit 12 in association with the measurement subject specification information of the measurement subject and the measurement date/time information (time stamp) (step S66).

The content shown in FIG. 6(B), for example, is stored in the storage unit 12 after the processing operations for personal authentication are performed. That is to say, in FIG. 6(B), it is specified that among the registered pieces of measurement subject specification information shown in FIG. 6(A), the measurement subject specification information corresponding to the measurement subject that was measured in the current instance of measurement corresponds to registration number 1, and the body information (body weight and body composition) is updated so as to be the body information obtained in the current instance of measurement with respect to registration number 1. Regarding registration number 2, the body information is not updated and is kept as it was before measurement, as shown in FIG. 6(A), since it was specified that registration number 2 does not correspond according to the processing operation of the current instance of specification. Note that registration numbers 3 and 4 remain unregistered, and the fields for body information and personal information are blank. The fields for body information and personal information are blank for the guest as well.

9) If the measurement subject switches off the power supply switch 15a of the body weight/body composition meter 10 or the control unit 11 detects that an input operation has not been performed for a predetermined amount of time or longer, the control unit 11 switches off the power supply of the body weight/body composition meter 10. As a result, the processing operation for personal authentication, in which measurement subject specification information corresponding to the measurement subject who was subjected to the current instance of measurement is specified from among the registered pieces of measurement subject specification information, ends.

Thus, according to the body weight/body composition meter 10 that includes the personal authentication apparatus 1, based on the personal information input using the first operation unit 15c and on the measurement results for the body weight and body impedance of the measurement subject that were measured and acquired respectively by the body weight measurement unit 17 and the body impedance measurement unit 16 serving as acquisition units, the control unit 11 serving as a calculation unit calculates a calculation value relating to body composition that is less susceptible to temporal variation than the body water amount. The storage unit 12 stores the body weight, the personal information, and the calculation value in association with the measurement subject specification information that specifies the measurement subject. The control unit 11 serving as a comparison unit obtains the difference between calculation values by comparing a calculation value that was most recently stored, and a new calculation value that was newly acquired according to the current instance of measurement. Also, based on the difference in calculation values, the control unit 11 functioning as a measurement subject specification unit specifies which of the pieces of measurement subject specification information that have already been stored in the storage unit 12 correspond to the results of the current instance of measurement that were measured and obtained by the body impedance measurement unit 16 and the body weight measurement unit 17 serving as acquisition units. An individual is authenticated (specified) using the specified measurement subject specification information.

Since the target of comparison in the body weight/body composition meter 10 that includes the personal authentication apparatus 1 is a calculation value relating to body composition that is less susceptible to temporal variation than the body water amount, temporal variation is less likely to occur and it is possible to perform personal recognition at a higher accuracy than in the case where the target of comparison is the body weight and the body impedance, which are likely to vary over a short amount of time such as a day or a week due to the influence of the body water amount.

Case of being recognized as a guest

The following describes processing operations in which the control unit 11 recognizes the measurement subject who was subjected to the current instance of measurement as a guest by determining that the body information, such as the body weight and body composition of the measurement subject, that was obtained using the current instance of measurement does not correspond to any of the pieces of body information registered in the storage unit 12. Also, a description will be given using a numerical value as an example that facilitates understanding of the invention and does not limit the invention, and a body weight of 65.25 kg and a body impedance of 510 Ω can be used as exemplary numerical values. Also, the threshold value for the body weight difference is 10 kg, for example.

Figure 5:
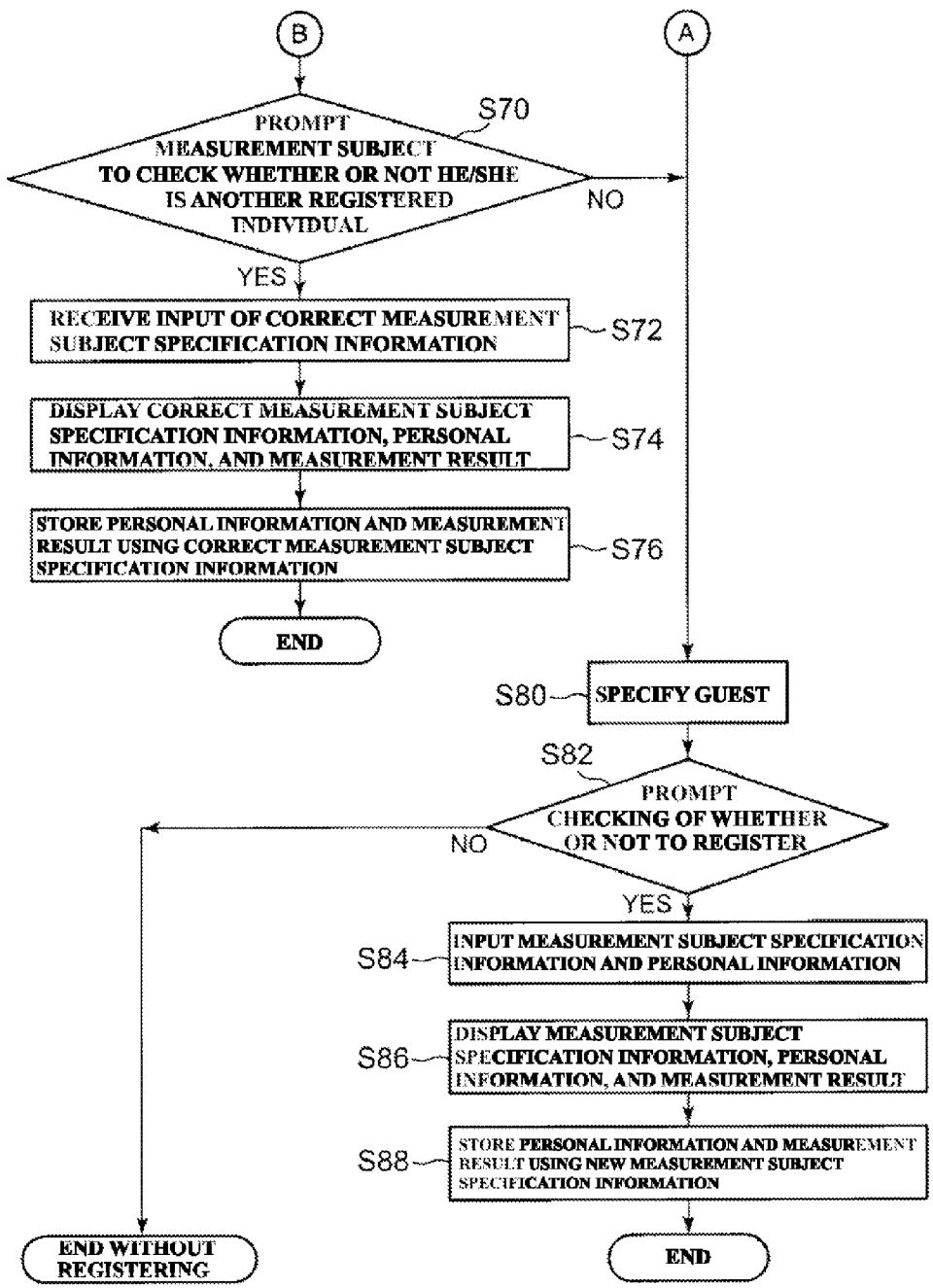
FIG. 5 is a diagram showing an operational flow that follows operational flow shown in FIG. 4.

10) If the control unit 11 determines in step S52 that the difference between the registered body weight and the body weight measured in the current instance is greater than or equal to a threshold value, the control unit 11 specifies that the current measurement subject is unregistered (a guest), as shown in step S80 in FIG. 5.

11) The control unit 11 serving as the display control unit causes the display unit 14 to display a confirmation screen to prompt the measurement subject to check whether or not the current measurement subject that has been specified as being unregistered (a guest) is to be newly registered (step S82).

12) If input for newly registering the current measurement subject who was specified as being unregistered (a guest) is received from the operation unit 15 in step S82, the control unit 11 serving as the display control unit causes the display unit 14 to display a confirmation screen to prompt the measurement subject to input his/her measurement subject specification information and personal information (age, height, and sex) (step S84).

Figure 7C:
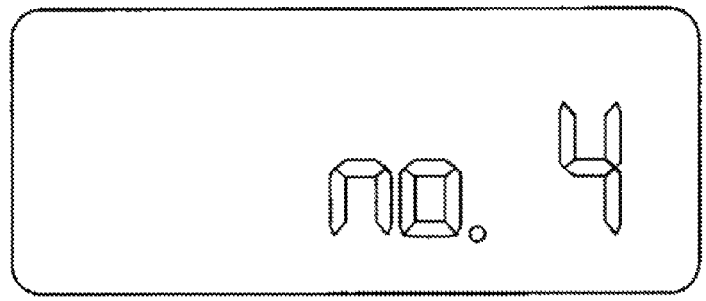
Figure 7D:
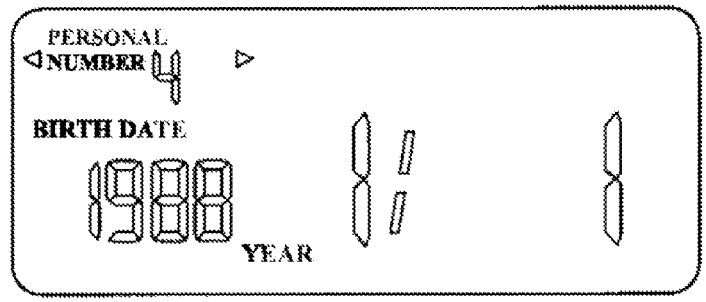

13) If input of the measurement subject specification information and the personal information (age, height, and sex) are received from the operation unit 15, the control unit 11 serving as the display control unit causes the display unit 14 to display the input measurement subject specification information, the personal information (age, height, and sex), and/or the measurement result (typically body weight) for confirmation (step S86). For example, a screen such as that shown in FIGS. 7(C) and (D) is displayed. FIG. 7(C) shows that the registration number (personal number) serving as the measurement subject specification information is 4. FIG. 7(D) shows that the birth date of the individual of registration number 4 is Jan. 1, 1988.

14) The control unit 11 stores the measurement subject specification information of the newly-registered measurement subject in the storage unit 12 in association with the body information, such as the body weight and body composition of the measurement subject that were acquired in the current instance, the personal information (age, height, and sex), and the measurement date/time information (time stamp) (step S88).

After the processing operation in which the measurement subject specification information corresponding to the measurement subject who was subjected to the current instance of measurement is newly registered has been performed, the storage unit 12 stores the content shown in FIG. 6(C), for example, separately from the registered measurement subject specification information. That is to say, in FIG. 6(C), the body information is not updated, and the body information remains as it was before measurement, as shown in FIG. 6(A), based on the fact that the control unit 11 has specified that registration numbers 1 and 2 do not correspond to the measurement subject who was subjected to the current instance of measurement. Registration number 4 is selected from among the unregistered registration numbers 3 and 4, and registration number 4 is newly registered. That is to say, body information such as the body weight and body composition of the measurement subject that were acquired in the current instance, the personal information (age, height, and sex), and the measurement date/time information (time stamp) are stored in the storage unit 12 in association with each other with respect to registration number 4. Note that registration number 3 remains unregistered, and the fields for body information and personal information are blank. The fields for body information and personal information are blank for the guest as well.

15) If the measurement subject switches off the power supply switch 15a of the body weight/body composition meter 10 or the control unit 11 detects that an input operation has not been performed for a predetermined amount of time or longer, the control unit 11 switches off the power supply of the body weight/body composition meter 10. As a result, the processing operation in which the measurement subject specification information corresponding to the measurement subject who was subjected to the current instance of measurement is newly registered separately from the registered measurement subject specification information ends.

Accordingly, even if the result of personal authentication is that the measurement subject who was subjected to the current instance of measurement is unregistered (a guest), he or she can be newly registered as necessary, and therefore a task of re-measurement after switching off the power and registering personal information is not necessary, and an effect of improving user-friendliness is achieved.

Immediately before the processing operation in which the current measurement subject who has been specified as being unregistered (a guest) is prevented from being registered, the storage unit 12 stores the content shown in FIG. 6(D), for example. That is to say, in FIG. 6(D), based on the fact that the control unit 11 has specified that registration numbers 1 and 2 do not correspond to the measurement subject who was subjected to the current instance of measurement, the body information thereof is not updated, and the body information thereof remains as it was before measurement, as shown in FIG. 6(A). Registration number 3 is left unregistered, and the fields for body information and personal information are blank. Registration number 4 is newly registered. Body information such as the body weight and body composition of the measurement subject acquired in the current instance, and the personal information (age, height, and sex) are temporarily stored in the storage unit 12 with respect to the unregistered individual (the guest).

16) If input by which the current measurement subject who has been specified as being unregistered (a guest) is prevented from being registered is received from the operation unit 15 in step S82, the control unit 11 deletes the body information such as the body weight and body composition acquired in the current instance and the personal information (age, height, and weight) of the measurement subject, which were temporarily stored in the storage unit 12.

17) If the measurement subject switches off the power supply switch 15a of the body weight/body composition meter 10 or the control unit 11 detects that an input operation has not been performed for a predetermined amount of time or longer, the control unit 11 switches off the power supply of the body weight/body composition meter 10. As a result, the processing operation in the case of determining that the measurement subject who was subjected to the current instance of measurement is unregistered (a guest) ends.

Accordingly, in the case where the result of personal authentication is that the measurement subject who was subjected to the current instance of measurement is unregistered (a guest), the body information, such as the body weight and the body composition that were acquired in the current instance, and the personal information (age, height, and sex) of the measurement subject are deleted from the storage unit 12, thereby achieving an effect of being able to prevent updating using incorrect information and storage of incorrect information, removing the risk of being confused with other information, and improving the reliability of the body weight/body composition meter 10.

18) If input such that the specified measurement subject specification information is incorrect is received from the operation unit 15 in step S62, the control unit 11 serving as the display control unit causes the display unit 14 to display a confirmation screen to prompt the measurement subject to check whether or not the current measurement subject is another registered individual (step S70). For example, a confirmation screen such as "GUEST?" is displayed.

19) If input such that the measurement subject who was subjected to the current instance of measurement is not another individual among the registered individuals is received from the operation unit 15 in step S70, the control unit 11 specifies that the current measurement subject is unregistered (a guest) similarly to step S80 above and performs the processing operation in accordance with the operation flow defined in 11) to 17) above.

20) If input such that the measurement subject who was subjected to the current instance of measurement corresponds to measurement subject specification information other than the measurement subject specification information specified by the control unit 11 among the registered pieces of measurement subject specification information is made via the operation unit 15 in step S72, the control unit 11 serving as the display control unit causes the display unit 14 to display a confirmation screen to prompt the measurement subject to input the correct measurement subject specification information (step S72) For example, a confirmation screen such as "INPUT YOUR No." is displayed.

21) In order to check whether or not the measurement subject specification information input in step S72 is correct, the control unit 11 serving as the display control unit causes the display unit 14 to display the specified measurement subject specification information, the personal information, and/or the measurement result (typically body weight) (step S74).

22) The control unit 11 stores the body information such as the body weight and body composition of the measurement subject that was acquired in the current instance of measurement in the storage unit 12 in association with the measurement subject specification information that was correctly specified, and the measurement date/time information (time stamp) (step S76).

23) If the measurement subject switches off the power supply switch 15a of the body weight/body composition meter 10 or the control unit 11 detects that an input operation has not been performed for a predetermined amount of time or longer, the control unit 11 switches off the power supply of the body weight/body composition meter 10. As a result, the processing operation for personal authentication in the personal authentication apparatus 1, in which measurement subject specification information corresponding to the measurement subject who was subjected to the current instance of measurement is correctly specified from among the registered pieces of measurement subject specification information, ends.

Note that control for the above-described personal authentication performed by the body weight/body composition meter 10 can be performed with a separate information processing apparatus (not shown), over a server for example, or with an information processing terminal apparatus such as a personal computer, a PDA (Personal Digital Assistant), a smartphone, a tablet, or the like. The control for personal authentication is performed via the communication unit 22. If control for personal authentication is to be performed with a separate information processing apparatus, application software can be recorded on various types of recording media, such as CDs, DVDs, and flash memories.

REFERENCE SIGNS LIST

Personal authentication apparatus
10 Body weight/body composition meter
11 Control unit
12 Storage unit
14 Display unit
15 Operation unit
15b First operation unit
15c Second operation unit
16 Body impedance measurement unit (acquisition unit)
17 Body weight measurement unit (acquisition unit)

The invention claimed is:

1. A personal authentication apparatus comprising:
first one or more electrodes configured to apply a current to a body;
second one or more electrodes configured to measure a voltage derived from the body at a time of applying the current;
a memory; and
a processor configured to:
acquire, from the second one or more electrodes, body weight and body impedance of a measurement subject;
perform an operation of inputting personal information that includes at least one of age, height, and sex that are specific to the measurement subject;
based on measurement results including the acquired body weight and the acquired body impedance, and the input personal information, calculate a calculation value relating to body composition that is less susceptible to temporal variation than body water amount;
store, in the memory, at least the acquired body weight, the input personal information, and the calculation value in association with measurement subject specification information that specifies the measurement subject;
compare a calculation value that was most recently stored in the memory and a new calculation value that is newly calculated; and
based on a difference between calculation values obtained by comparing the most recently stored calculation value and the new calculation value, specify which of the pieces of measurement subject specification information stored in the memory corresponds to the acquired measurement result.

2. The personal authentication apparatus according to claim 1, wherein a plurality of pieces of the measurement subject specification information are stored in the memory.

3. The personal authentication apparatus according to claim 2, wherein the processor is further configured to select the measurement subject specification information corresponding to the calculation value with the smallest difference.

4. The personal authentication apparatus according to claim 1, wherein the processor is further configured to, in the case of no specification by the measurement subject specification unit, delete the corresponding body weight, personal information, and calculation value from the memory.

5. The personal authentication apparatus according to claim 1, wherein the calculation value relating to the body composition is obtained by subtracting fat-free mass from the acquired body weight.

6. The personal authentication apparatus according to claim 1, wherein the calculation value relating to the body composition is a muscle mass value.

7. A personal authentication apparatus comprising:
a memory; and
a processor configured to:
acquire body weight and body impedance of a measurement subject;
perform an operation of inputting personal information that includes at least one of age, height, and sex that are specific to the measurement subject;
based on measurement results including the acquired body weight and the acquired body impedance, and the input personal information, calculate a calculation value relating to body composition that is less susceptible to temporal variation than body water amount;
store, in the memory, at least the acquired body weight, the input personal information, and the calculation value in association with measurement subject specification information that specifies the measurement subject;
compare a calculation value that was most recently stored in the memory and a new calculation value that is newly calculated; and
based on a difference between calculation values obtained by comparing the most recently stored calculation value and the new calculation value, specify which of the pieces of measurement subject specification information stored in the memory corresponds to the acquired measurement result; and
a display or display screen configured to display the measurement subject specification information, wherein the processor is further configured to perform control such that the measurement subject specification information is displayed on the display or display screen.

8. The personal authentication apparatus according to claim 7, wherein the processor is further configured to:
cause the display or display screen to display confirmation information to prompt checking of correctness with regard to the measurement subject specification information, and
perform an operation of input as to whether to accept or correct the measurement subject specification information, based on the confirmation information displayed on the display unit.

9. A body weight/body composition meter comprising the personal authentication apparatus according to claim 1.

* * * * *